United States Patent [19]

Walz et al.

[11] 4,237,268
[45] Dec. 2, 1980

[54] ESTERS OF ACYLATED AMINOCARBOXYLIC ACID CONTAINING COMPOUNDS

[75] Inventors: Klaus Walz; Ergun Tamer, both of Leverkusen, Fed. Rep. of Germany

[73] Assignee: Bayer Aktiengesellschaft, Leverkusen, Fed. Rep. of Germany

[21] Appl. No.: 925,885

[22] Filed: Jul. 18, 1978

[30] Foreign Application Priority Data

Jul. 19, 1977 [DE] Fed. Rep. of Germany ....... 2732557

[51] Int. Cl.$^3$ .................... C07H 13/02; C07H 11/00; C07C 101/30; C07C 125/06
[52] U.S. Cl. ......................... 536/4; 536/53; 536/119; 536/115; 560/32; 560/39; 560/41; 560/43; 560/125; 560/166; 560/172
[58] Field of Search ..................... 536/53, 4, 115, 119; 260/553; 560/32, 39, 41, 43, 125, 166, 172

[56] References Cited

U.S. PATENT DOCUMENTS

| 2,146,873 | 2/1939 | Wilmanns et al. | 536/53 |
|---|---|---|---|
| 2,216,617 | 10/1940 | Katz | 536/53 |
| 2,229,744 | 1/1941 | Kern | 536/53 |
| 2,355,911 | 8/1944 | Graenacher et al. | 536/53 |
| 2,374,236 | 4/1945 | Salzberg et al. | 536/53 |
| 2,612,497 | 9/1952 | Meijer | 536/53 |
| 2,776,241 | 1/1957 | Priewe et al. | 536/53 |
| 2,805,219 | 9/1957 | Kagan et al. | 536/53 |
| 2,809,190 | 10/1957 | Kelly et al. | 536/53 |
| 2,895,988 | 7/1959 | Archer et al. | 536/53 |
| 2,993,887 | 7/1961 | Zech | 536/53 |
| 3,051,745 | 8/1962 | Obendorf | 536/53 |
| 3,086,010 | 4/1963 | Matthaeus et al. | 536/53 |

*Primary Examiner*—Johnnie R. Brown
*Attorney, Agent, or Firm*—Sprung, Felfe, Horn, Lynch & Kramer

[57] ABSTRACT

Surface-active esters of aliphatic polyols containing at least 3 hydroxyl groups and aliphatic, cycloaliphatic or araliphatic acylaminocarboxylic acids, which contain a total of at least 8, preferably 12–60, carbon atoms and which are acylated by aliphatic carboxylic acids with 1–4 carbon atoms, aromatic or araliphatic carboxylic acids or aliphatic, aromatic or araliphatic sulphonic, carbonic or carbamic acids, are suitable as auxiliaries in the dyeing of textile materials.

4 Claims, No Drawings

ESTERS OF ACYLATED AMINOCARBOXYLIC ACID CONTAINING COMPOUNDS

The invention relates to surface-active esters of aliphatic polyols containing at least 3 hydroxyl groups and aliphatic, cycloaliphatic or araliphatic acylaminocarboxylic acids, which contain a total of at least 8, preferably 12-60, carbon atoms and which are acylated by aliphatic carboxylic acids with 1-4 carbon atoms, aromatic or araliphatic carboxylic acids or aliphatic, aromatic or araliphatic sulphonic, carbonic or carbamic acids, a process for their preparation and their use as auxiliaries in the dyeing of textile materials.

Preferred esters according to the invention are derived from carboxylic acids of the formula

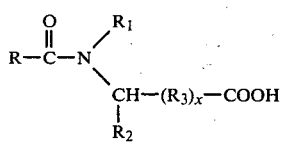

in which

R represents H, $C_1$-$C_4$-alkyl, $C_1$-$C_{22}$-alkoxy, $C_3$-$C_{22}$-alkenoxy, aryl, aralkyl, aroxy, aralkoxy or the radical

$R_1$, $R_4$ and $R_5$ represent H, $C_1$-$C_{22}$-alkyl, $C_3$-$C_{22}$-alkenyl, cycloalkyl, aryl or aralkyl, or $R_5$ represents a radical

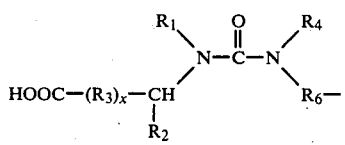

in which $R_6$ = a divalent organic radical.

$R_2$ represents H, COOH, COO $C_1$-$C_4$-alkyl or $C_1$-$C_6$-alkyl, $R_3$ represents $C_1$-$C_{10}$-alkylene and x represents 0 or 1, and wherein at least one of the radicals $R_1$ to $R_5$ contains at least 6 carbon atoms, the alkyl, alkenyl and cyclic radicals can carry substituents and the total number of carbon atoms is 20-60, if $R_5$ is substituted by the urea radical given, and 12-30 for all other cases.

In particular, by aryl there are to be understood phenyl and naphthyl, by cycloalkyl there are to be understood cyclohexyl, tetrahydronaphtyl, decahydronaphthyl and abietyl, and by aralkyl there are to be understood benzyl, phenylethyl and naphthylmethyl.

These radicals can carry further substituents. The rings mentioned can preferably carry 1 or 2 substituents, such as halogen, in particular chlorine or bromine, cyano, carboxyl, $C_1$-$C_4$-alkoxycarbonyl, carbamoyl, $C_1$-$C_4$-alkoxy, $C_1$-$C_4$alkyl, benzyl or phenyl.

The alkyl and alkenyl radicals of the compounds (I) can be substituted by 1-3 further radicals, such as halogen, for example fluorine, chlorine or bromine, cyano, carboxyl, $C_1$-$C_4$-alkoxycarbonyl, carbamoyl or $C_1$-$C_4$-alkoxy.

The radical $R_6$ preferably represents $C_2$-$C_8$-alkylene or a radical of the formulae

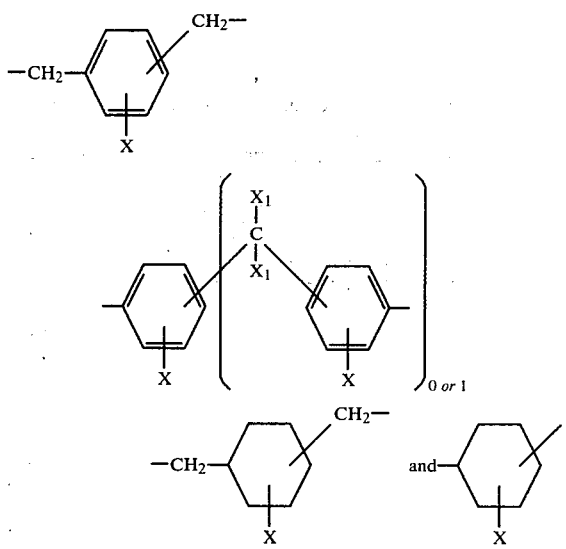

X and $X_1$ = hydrogen or $C_1$-$C_4$-alkyl

Examples which may be mentioned of aliphatic polyols containing at least 2 hydroxyl groups are: glycerol, erythritol, erythrose, pentoses or hexoses, such as arabinose, xylose, glucose, fructose, galactose or mannose, pentitols or hexitols, such as arabitol, xylitol, mannitol, sorbitol or dulcitol, disaccharides or oligosacccarides, such as maltose, sucrose or hydroylsis products of polysaccharides, as well as polysaccharides, such as dextrin or starch. Examples of further suitable polyols are synthetic sugar compounds of the formose type, polyvinyl alcohols and derivatives of the abovementioned polyols, such as alkyl- or hydroxylalkyl-glycosides, hydroxyalkyl ethers or partial esters or ethers of polyhydroxy compounds.

The surface-active esters can be prepared in a manner which is in itself known by two different processes.

PROCESS A

In this process, the acylated aminocarboxylic acid, or a derivative of such an acid, is reacted with an aliphatic polyol, optionally in the presence of acid or basic catalysts. Chlorides or lower alkyl esters, in particular methyl and ethyl esters, are employed as derivatives of the carboxylic acids. The methyl or ethyl esters of the carboxylic acids (I) are preferably employed. The carboxylic acids (I) and their derivatives can be prepared by known processes, for example by acylating aminoacids or aminoacid esters with customary acylating agents, such as isocyanates, carboxylic acid anhydrides or carboxylic acid halides or chloroformic acid esters.

PROCESS B

In this process, esters of aminocarboxylic acids which still contain at least one hydrogen atom on the nitrogen, and aliphatic polyols containing at least 3 hydroxyl groups are reacted with acylating agents, and the sum of the carbon atoms in the aminocarboxylic acid radical and in the acyl radical of the acylating agent should be at least 8, preferably 10–22. Esters of aminocarboxylic acids of the formula

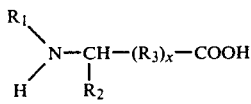 (II)

wherein $R_1$, $R_2$, $R_3$ and x have the meaning given in formula (I), are preferably reacted.

The acylation can be carried out with customary acylating agents, such as carboxylic acid esters, carboxylic acid anhydrides or carboxylic acid halides, chloroformic acid esters, sulphonic acid chlorides or, preferably, with organic monoisocyanates or diisocyanates, optionally in the presence of catalysts or molar amounts of acid acceptors.

The process conditions of the two Preparation Processes A and B can vary within wide limits. The properties of the esters prepared can be varied by choosing the molar ratio between the aminocarboxylic acid or acylaminocarboxylic acid and the aliphatic polyols.

In general, 0.5–2.0, preferably 0.8–1.2, mols of aliphatic polyol are employed per equivalent of carboxyl group.

The reaction according to Process A can be carried out with or without the addition of solvents, at temperatures of 20°–180° C., preferably at 70°–140° C. In the case of the lower alkyl esters of the aminocarboxylic acids or acylaminocarboxylic acids, which are preferably employed, the customary solvents, such as xylene, dimethylformamide, dimethylsulphoxide, N-methylpyrrolidine or dimethylacetamide can be used. In this case, it is advisable to add acid or, in particular, basic catalysts to the reaction mixture in amounts of 0.5–20% (relative to the carboxylic acid). Examples of suitable acid catalysts are hydrogen chloride, sulphuric acid, toluenesulphonic acid or acid ion exchangers. Basic catalysts which can be used are alkali metal hydroxides, carbonates or alcoholates or alkaline earth metal hydroxides, carbonates or alcoholates, as well as organic bases. The acylation reaction according to Process B is carried out at 0° to 120° C., preferably at 20° to 90° C., optionally in solvents, such as lower alcohols, glycols, ketones, aromatic hydrocarbons, carboxylic acid esters or carboxylic acid amides.

Of the acids of the formula (I), the acids of the formula

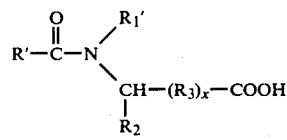 (III)

in which

R' represents hydrogen, $C_1$–$C_4$-alkyl, $C_1$–$C_{22}$-alkoxy $C_3$–$C_{22}$-alkenyloxy, phenyl, naphthyl, benzyl, phenylethyl, naphthylmethyl, phenoxy, benzoxy, phenylethoxy or a radical

$R_1'$, $R_4'$ $R_5'$ represent hydrogen, $C_1$–$C_{22}$-alkyl, $C_3$–$C_{22}$-alkenyl, cyclohexyl, tetrahydronaphtyl, decahydronaphthyl, abietyl, phenyl, naphthyl, benzyl or phenylethyl or $R_5'$ represents a radical of the formula

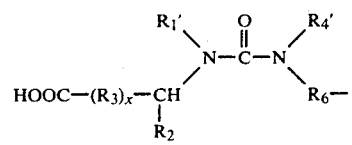

in which $R_2$, $R_3$, $R_6$ and x have the abovementioned meaning, at least one of the radicals, $R_1'$, $R_2$, $R_3$, $R_4'$ and $R_5'$ contain at least 6 carbon atoms and the alkyl, alkenyl and cyclic radicals can be substituted by fluorine, chlorine, bromine, cyano, carboxyl, $C_1$–$C_4$-alkoxycarbonyl, carbamoyl or $C_1$–$C_4$-alkoxy and the cyclic radicals can also be substituted by $C_1$–$C_4$-alkyl, are preferred.

Preferred esters according to the invention are prepared, according to Process A, by reacting lower alkyl esters, in particular methyl esters, of acylaminocarboxylic acids of the formula

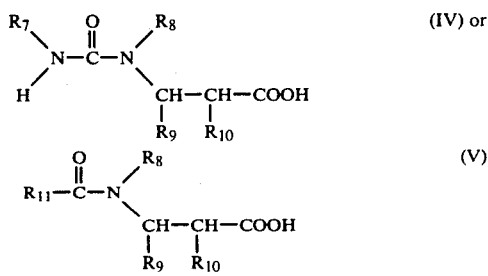

wherein $R_7$ represents $C_1$–$C_{22}$-alkyl, $C_3$–$C_{22}$-alkenyl, cyclohexyl, tetrahydronaphthyl, decahydronaphthyl, abietyl, phenyl, naphthyl, benzyl, phenylethyl or a radical of the formula

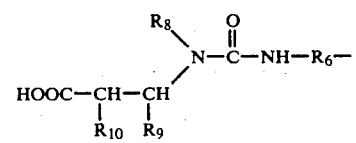

wherein $R_6$ has the meaning indicated in formula (I), $R_8$ represents hydrogen, $C_1$–$C_{22}$-alkyl, $C_3$–$C_{22}$-alkenyl, cyclohexyl, tetrahydronaphthyl, decahydronaphthyl, abietyl, benzyl or phenylethyl, $R_9$ represents hydrogen or carboxyl and $R_{10}$ and $R_{11}$ represent hydrogen or methyl, at least one of the radicals $R_7$ or $R_8$ has at least 8 carbon atoms and the alkyl, alkenyl and cyclic radicals can carry the substituents mentioned in formula (III), with aliphatic polyols containing at least 6 carbon atoms.

Sorbitol, glucose, alkyl- or hydroxyalkyl-glycosides, trehalose, raffinose, sucrose or mixtures thereof, and in particular sucrose, are preferably used here.

The preferred esters can also be prepared by Process B by reacting esters of aminocarboxylic acids of the formula $$R_8-NH-CH-CH-COOH \quad \text{(VI)}$$
$$\phantom{R_8-NH-}R_9 \phantom{-}R_{10}$$

and aliphatic polyols containing at least 6 carbon atoms with isocyanates of the formula $$R_7-N=C=O$$

wherein $R_7 - R_{10}$ have the abovementioned meaning, or with methyl formate, acetyl chloride or acetic anhydride. Examples of isocyanates which may be mentioned are: methyl, ethyl, propyl, butyl, hexyl, 6-chlorohexyl, octyl, decyl, dodecyl, hexadecyl, octadecyl, cyclohexyl, phenyl, naphthyl and allyl isocyanate, as well as butylene, hexamethylene, phenylene, toluylene and hexahydrophenylene diisocyanate.

The aminocarboxylic acid esters which are used are preferably those esters which are based on those aminocarboxylic acids of the formula $$R_{12}-NH-CH-COOH \quad \text{(VII) or}$$
$$\phantom{R_{12}-NH-}CH_2-COOH$$

$$R_{12}-NH-CH_2-CH-COOH \quad \text{(VIII)}$$
$$\phantom{R_{12}-NH-CH_2-}R_{10}$$

wherein $R_{10}$ has the abovementioned meaning and $R_{12}$ represents $C_1$-$C_{22}$-alkyl or $C_3$-$C_{22}$-alkenyl, and the aliphatic polyols sorbitol, glucose, alkyl- or hydroxyalkyl-glycosides, trehalose, raffinose or, in particular, sucrose.

Particularly preferred esters according to the invention are esters of acylaminocarboxylic acids of the formulae

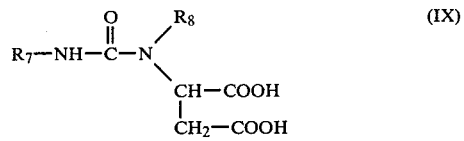

and 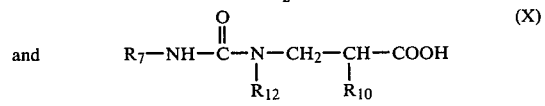

wherein $R_7$, $R_8$, $R_{10}$ and $R_{12}$ have the abovementioned meaning, and sucrose.

Examples of suitable carboxylic acids of the formula (I) are:

| R | | $R_1$ | $R_2$ | $R_3$ | x |
|---|---|---|---|---|---|
| H | | $C_{12}H_{25}$ | H | $CH_2$ | 1 |
| $CH_3$ | | $C_{12}H_{25}$ | H | $CH_2$ | 1 |
| $CH_3$ | | $C_{12}H_{25}$ | H | CH<br>\|<br>$CH_3$ | 1 |
| $CH_3$ | | $C_{16}H_{33}$ | H | $CH_2$ | 1 |
| $CH_3$ | | $C_{16}H_{33}$ | COOH | $CH_2$ | 1 |
| C<sub>6</sub>H<sub>5</sub>— | | $C_{12}H_{25}$ | COOH | $CH_2$ | 1 |
| Cl—C<sub>6</sub>H<sub>4</sub>— | | $C_{10}H_{21}$ | H | CH<br>\|<br>$CH_3$ | 1 |
| $CH_3-O$ | | $C_{14}H_{29}$ | H | $CH_2$ | 1 |
| $C_4H_9-O$ | | $C_{12}H_{25}$ | H | — | 0 |
| $C_{10}H_{21}-O$ | | cyclohexyl | COOH | $CH_2$ | 1 |
| $C_{18}H_{35}-O$ | | $CH_3$ | COOH | $CH_2$ | 1 |
| $ClCH_2CH_2-O$ | | $C_{18}H_{37}$ | COOH | $CH_2$ | 1 |
| $CH_3-O$ | | abietyl | H | $CH(H_3)$ | 1 |
| C<sub>6</sub>H<sub>5</sub>—CH<sub>2</sub>—O | | $C_{12}H_{25}$ | COOH | $CH_2-CH_2$ | 1 |
| $CH_3-NH$ | | $C_{12}H_{25}$ | COOH | $CH_2$ | 1 |
| $CH_3-NH$ | | $C_{16}H_{33}$ | H | $CH_2$ | 1 |
| $CH_3-NH$ | | $C_{18}H_{37}$ | H | $CH(CH_3)$ | 1 |
| $CH_3-NH$ | | abietyl | COOH | $CH_2$ | 1 |
| $CH_3-NH$ | | $C_{12}H_{25}$ | n-$C_6H_{13}$ | — | 0 |
| n-$C_4H_9-NH$ | | $C_{12}H_{25}$ | COOH | $CH_2$ | 1 |
| n-$C_4H_9-NH$ | | $C_{14}H_{29}$ | COOH | $CH_2$ | 1 |
| iso-$C_4H_9-NH$ | | $C_{18}H_{35}$ | COOH | $CH_2$ | 1 |
| iso-$C_4H_9-NH$ | | $C_{18}H_{37}$ | H | $(CH_2)_3$ | 1 |
| Cl—$(CH_2)_6-NH$ | | $C_{10}H_{21}$ | COOH | $CH_2$ | 1 |
| Cl—$(CH_2)_6-NH$ | | abietyl | COOH | $CH_2$ | 1 |
| HOOC—CH<sub>2</sub>CH<sub>2</sub>—N(C<sub>12</sub>H<sub>25</sub>)—C(O)—NH(CH<sub>2</sub>)<sub>6</sub>—NH | | $C_{12}H_{25}$ | H | $CH_2$ | 1 |
| $C_{12}H_{25}-NH$ | | $CH_3$ | COOH | $CH_2$ | 1 |
| $C_{12}H_{25}-NH$ | | $CH_2=CH-CH_2$ | COOH | $CH_2$ | 1 |

-continued

| R | R₁ | R₂ | R₃ | x |
|---|---|---|---|---|
| $C_{12}H_{25}$—NH | ⟨H⟩— (phenyl) | H | $CH_2$ | 1 |
| $C_{12}H_{25}$—NH | ⟨⟩—$CH_2$ (benzyl) | COOH | $CH_2$ | 1 |
| $C_{12}H_{25}$—NH | H | H | $(CH_2)_4$ | 1 |
| $C_{12}H_{25}$—NH | $C_{12}H_{25}$ | COOH | $CH_2$ | 1 |
| $C_{14}H_{29}$—NH | $CH_3$ | COOH | $CH_2$ | 1 |
| $C_{14}H_{29}NH$ | ⟨⟩— (phenyl) | H | $CH_2$ | 1 |
| $C_{14}H_{29}NH$ | Cl—⟨⟩— | H | — | 0 |
| $C_{16}H_{33}NH$ | ⟨H⟩— | COOH | $CH_2$ | 1 |
| $C_{18}H_{37}NH$ | $C_4H_9$ | COOH | $CH_2$ | 1 |
| $C_{18}H_{37}$—NH | $CH_3$ | $COOCH_3$ | $CH_2$ | 1 |
| | $C_8H_{17}$ | COOH | $CH_2$ | 1 |
| ⟨⟩—NH | H | H | $(CH_2)_9$ | 1 |
| Cl—⟨⟩—NH | $C_{12}H_{25}$ | H | $CH(CH_3)$ | 1 |
| $CH_3$—⟨⟩—NH | $C_{12}H_{25}$ | COOH | $CH_2$ | 1 |
| ⟨⟩—NH | $C_{16}H_{33}$ | COOH | $CH_2$ | 1 |
| ⟨⟩—NH | $C_{18}H_{37}$ | COOH | $CH_2$ | 1 |
| ⟨H⟩—NH | $C_{18}H_{37}$ | H | — | 0 |
| ⟨H⟩—NH | | | | |
| abietyl-NH | $CH_3$ | COOH | $CH_2$ | 1 |
| COOH  COOH       O<br>  \|         \|               \|\|<br>$CH_2$—CH—N—C—NH—⟨⟩—NH<br>              \|<br>           $C_{12}H_{25}$        $CH_3$ | $C_{12}H_{25}$ | COOH | $CH_2$ | 1 |
| COOH  COOH       O<br>  \|         \|               \|\|<br>$CH_2$—CH—N—C—NH—⟨⟩—NH<br>              \|<br>           $C_{18}H_{37}$ | $C_{18}H_{37}$ | COOH | $CH_2$ | 1 |
| COOH  COOH       O<br>  \|         \|               \|\|<br>$CH_2$—CH—NH—C—NH—$(CH_2)_6$—NH | $C_{18}H_{37}$ | COOH | $CH_2$ | 1 |
| $\quad\quad\quad\quad\quad\quad O$<br>$\quad\quad\quad\quad\quad\quad \|\|$<br>HOOC—CH—$CH_2$—NH—C—NH—$(CH_2)_6$—NH<br>            \|<br>         $CH_3$ | $C_{12}H_{25}$ | $CH_3$ | — | 0 |

The new compounds are surface active compounds which are fully degradable biologically, the properties of which can be varied within wide limits by choosing the starting materials and the proportions. The compounds can therefore be employed in the most diverse fields of use, for example as washing agents, cleaning agents or wetting agents, as emulsifiers, dispersing agents or thickeners and as dyeing and printing auxiliaries.

The new compounds are preferably suitable for use in the continuous dyeing or printing of fibre materials with dyestuffs which are customary for such fibres. The process consists in impregnating or printing the fibre materials with an aqueous liquor which contains the dyestuffs and the compounds according to the invention, and then subjecting the fibre materials to an after-treatment with heat.

The required amounts of the products according to the invention can be easily determined by preliminary experiments; in general, amounts of about 5-20 g per litre of padding liquor provided to be sufficient.

Possible dyestuffs for the process according to the invention are all the dyestuffs which are customarily used for dyeing and printing textile materials, for example acid dyestuffs, reactive dyestuffs, after-chroming dyestuffs, 1:1 and 1:2 metal complex dyestuffs, cationic dyestuffs, direct dyestuffs and disperse dyestuffs.

The following dyestuffs from the Colour Index, 3rd Edition, volume 5, are examples which are suitable: As acid dyestuffs: C.I. Acid Yellow 79, C.I. Acid Red 80, C.I. Acid Green 44 and C.I. Acid Red 111;
as after-chroming dyestuffs: C.I. Mordant Yellow 5, C.I.
Mordant Black 65 and C.I. Mordant Brown 21;
as 1:1 metal complex dyestuffs: C.I. Acid Yellow 54 and C.I. Acid Red 214;
as 1:2 metal complex dyestuffs: C.I. Acid Blue 199, C.I. Acid Red 277, C.I. Acid Brown 253, C.I. Acid Blue 151 and C.I. Acid Green 86;
as reactive dyestuffs: C.I. Reactive Blue 94, C.I. Reactive Red 100 and C.I. Reactive Yellow 69;
as cationic dyestuffs: C.I. Basic Yellow, 11, C.I. Basic Blue 3 and C.I. Basic Red 18;
as direct dyestuffs: C.I. Direct Orange 46 and C.I. Direct Blue 84; and
as disperse dyestuffs: C.I. Disperse Yellow 5, C.I. Disperse Yellow 60, C.I. Disperse Blue 73.

The dyeing and printing can be carried out, for example, in the following manner:

The dyestuffs are dispersed in water whilst stirring vigorously, optionally whilst warming to about 70°–80° C.; the compounds to be used according to the invention are then added and the resulting mixture is optionally acidified with lower aliphatic carboxylic acids, such as acetic acid, formic acid or oxalic acid, or compounds which split off acid under the action of heat, such as ammonium sulphate or ammonium acetate, are added. The fibre materials are impregnated with this liquor, for example on a padder, and then subjected to an after-treatment with heat. This can consist of a treatment at about 100°–110° C., in particular in the case of wool and polyacrylonitrile fibres, or of a dry heat treatment at temperatures from 120° to 220° C., in particular in the case of synthetic polyamide fibres and polyester fibres. After the heat treatment, the fibre material is washed, rinsed and dried.

The dyeings and prints can in many cases be further improved by co-using urea, thiourea or organic solvents which have a good solvent power for the particular dyestuff used; in this connection there may be mentioned, for example, butanol, hexanol, 2-ethylhexanol, cyclohexanol, benzyl alcohol, diethylene glycol, triethylene glycol, thiodiethylene glycol and the monoethyl ether and monobutyl ether of ethylene glycol or of diethylene glycol.

An improvement in the dyeing or print can in many cases also be achieved by co-using alkylsulphonamides and/or anionic compounds, for example alkyl-sulphates, alkylarylsulphonates, fatty acid salts or, preferably, alkylsulphonates, which can be employed as the sodium, potassium or ammonium salts or also as the mono-, di- or tri-ethanolamine salts.

Furthermore, in order to improve the uniformity of the dyeing, it is advisable to add an acid-resistant thickener to the padding liquors, for example a derivative of carob bean flour.

With the aid of the process according to the invention, it is possible to dye or print textile materials, for example flocks, tow, slivers, woven fabrics, knitted fabrics or fleeces made, for example, of natural and synthetic polyamides, polyesters or polyacrylonitrile, as well as cellulose fibres, and mixtures with one another.

A particular advantage of the process according to the invention is that it can be universally applied, that is to say all dyeable fibre materials can be dyed by the process.

The new compounds make excellent fixing of the dyestuffs possible. The resulting dyeings are distinguished by good fastness to wet processing, perspiration and rubbing.

The appearance of a frosting effect is prevented by the new compounds.

The parts given in the Examples which follow are parts by weight.

EXAMPLE 1

50 ml of dimethylformamide are distilled off from a solution of 136.8 parts of sucrose in 600 parts of dimethylformamide over a column at 90°–100° C. in vacuo in the course of 1–2 hours. 4 parts of potassium carbonate and 94 parts of an aspartic acid dimethyl ester of the formula

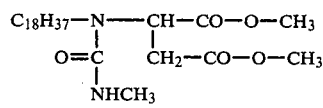

which has been prepared by reacting N-octadecylaspartic acid dimethyl ester with methyl isocyanate, are then added. About 100 parts of a mixture of methanol and dimethylformamide are then distilled off from the reaction mixture at 90°–100° C. and under about 100 mm Hg in the course of 6 hours, whilst stirring. The residue in the flask is freed from dimethylformamide at 100° C. and under a vacuum of up to 2 mm Hg. 237 parts of a brown resin are obtained, which solidifies in the cold to give a brittle, pulverisable resin. The product is soluble in water giving a clear solution, melts at 150°–160° C., has an OH number of 610 and a saponification number of 72 and lowers the surface tension of water to 46 dynes/cm in a 0.1% strength solution.

EXAMPLE 2

A solution of 136.8 parts of sucrose in 600 parts of dimethylformamide is reacted with 77.2 parts of an aspartic acid ester of the formula

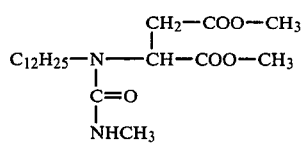

which has been prepared by reacting N-dodecylaspartic acid dimethyl ester with methyl isocyanate, in the presence of 2 parts of potassium carbonate under the conditions indicated in Example 1. After distilling off the dimethylformamide, 200 parts of a pulverisable resin which is brittle at room temperature are obtained. The product, which is soluble in water giving a clear solution, has an OH number of 650 and a saponification number of 78 and lowers the surface tension of water to 35 dynes/cm in a 0.1% strength solution.

EXAMPLE 3

A solution of 171 parts of sucrose in 650 parts of dimethylformamide is reacted with 108.8 parts of an aspartic acid ester of the formula

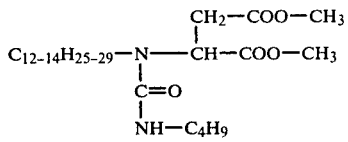

which has been prepared by reacting N-coconut fatty alkylaspartic acid dimethyl ester with n-butyl isocyanate, in the presence of 4 parts of potassium carbonate under the conditions indicated in Example 1. After distilling off the dimethylformamide, 278 parts of a resinous product which is soluble in water giving a clear solution, are obtained. The product has an OH number of 540 and a saponification number of 60 and lowers the surface tension of water of 33 dynes/cm in a 0.1% strength solution.

EXAMPLE 4

136.8 parts of sucrose and 2 parts of potassium carbonate in 600 parts of dimethylformamide are reacted with 100 parts of an aspartic acid ester of the formula

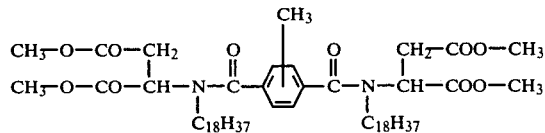

which has been obtained by reacting 207 parts of N-octadecylaspartic acid dimethyl ester with 30 parts of toluylene diisocyanate, in the manner described in Example 1. After removing the dimethylformamide in vacuo, 220 parts of a watersoluble, brittle, pulverisable resin are obtained.

The product has an OH number of 684 and a saponification number of 98.5 and lowers the surface tension of water to 52 dynes/cm in a 0.1% strength solution.

EXAMPLE 5

232 parts of sucrose and 2 parts of potassium carbonate in 630 parts of dimethylformamide are reacted with 152 parts of an aspartic acid ester of the formula

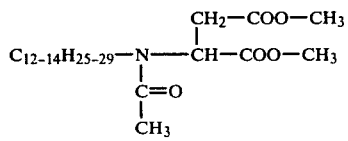

which has been prepared by reacting 168 parts of N-coconutalkyl-aspartic acid dimethyl ester with 66 parts of acetic anhydride, in the manner described in Example 1. After removing the dimethylformamide in vacuo, 350 parts of a product which solidifies to give a resin and is soluble in water giving a clear solution, are obtained.

It melts at 80°–84° C., has an OH number of 675 and a saponification number of 151 and lowers the surface tension of water to 30.5 dynes/cm in a 0.1% strength solution.

EXAMPLE 6

137 parts of sucrose and 2 parts of potassium carbonate in 450 parts of dimethylformamide are reacted with 110 parts of a reaction product of the formula

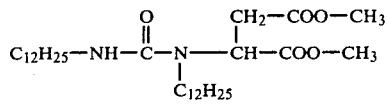

from 255 parts of N-dodecyl-aspartic acid dimethyl ester and 152 parts of n-dodecyl isocyanate in the manner described in Example 1. After removing the solvent in vacuo, 229 parts of a resinous, pulverisable product which is readily soluble in water, are obtained. It melts at 140°–145° C. and has a saponification number of 65 and a hydroxyl number of 660.

EXAMPLE 7

146 parts of sorbitol and 4 g of potassium carbonate in 550 parts of dimethylformamide are reacted with 160 parts of a reaction product from 1 mol of N-coconut alkyl-aspartic acid dimethyl ester and 1 mol of methyl isocyanate in the manner indicated in Example 1. After distilling off the dimethylformamide, 286 parts of a resin which is soluble in water giving a clear solution and solidifies to a sticky mass, are obtained. The product has a saponification number of 85 and a hydroxyl number of 826.

EXAMPLE 8

103 parts of sucrose and 2 parts of sodium methylate in 500 parts of dimethylformamide are reacted with 110 parts of the compound of the formula

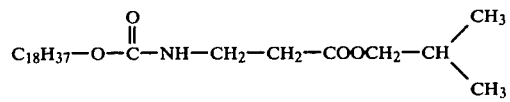

which has been prepared by reacting 3-isocyanatopropionic acid isobutyl ester with octadecyl alcohol, in the manner indicated in Example 1.

Instead of the methanol/dimethylformamide mixture, a mixture of isobutanol and dimethylformamide is distilled off in vacuo. After removing the solvent, 195 parts of a light brown, pulverisable resin are obtained. The product is soluble in warm water and lowers the surface tension of water to 55 dynes/cm in a 0.1% strength solution. The saponification number is 54 and the hydroxyl number is 630.

EXAMPLE 9

103 parts of sucrose and 4 parts of potassium carbonate in 500 parts of dimethylformamide are reacted with 103 parts of the compound of the formula

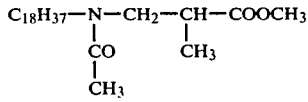

which has been obtained by reacting 3-octadecylamino-isobutyric acid with acetic anhydride, in the manner indicated in Example 1. After removing the solvent in vacuo, 198 parts of a water-soluble, brown resin are obtained. The product lowers the surface tension of water to 39.3 dynes/cm in a 0.1% strength solution. It has a hydroxyl number of 552 and a saponification number of 55.

EXAMPLE 10

20 parts of the dyestuff C.I. No. 61,590 (3rd edition, volume 4) are dissolved in 600 parts of soft water having a temperature of about 80° C.; 8 parts of the compound from Example 5 and 2 parts of sodium laurylsulphonate are then added, whilst stirring. The solution is added to 200 parts of a 4% strength aqueous formulation of a commercially available derivative of carob bean flour, whilst stirring continuously. Thereafter, 20 parts of acetic acid (60% strength) are added to the homogeneous solution. Finally, the dyestuff formulation is filled up to 1,000 parts with cold, soft water.

A wool sliver is impregnated with this dye liquor on a padder; the liquor pick-up here is about 100%. The sliver is then steamed continuously in a steamer for 15 minutes using saturated steam at 102°–103° C. Thereafter, the sliver is washed with warm water having a temperature of about 50° C. on a back-washer and acidified with acetic acid or formic acid.

An excellent green dyeing which has very good fastness to perspiration, washing and water and exhibits no frosting effect, is obtained.

EXAMPLE 11

600 parts of hot, soft water having a temperature of 80° C. are poured over 15 parts of the dyestuff C.I. 18,170 (3rd edition, volume 4); 10 parts of the compound from Example 3 are then added. The solution is added to 200 parts of a 4% strength aqueous formulation of a commercially available derivative of carob bean flour, whilst stirring vigorously. Thereafter, the solution is cooled to about 50° C. and a mixture of 20 parts of chromium fluoride, 30 parts of formic acid (8% strength) and 100 parts of hot water is added. Finally, the dyestuff formulation is filled up to 1,000 parts with cold, soft water.

A wool sliver is impregnated with the dye liquor obtained in this manner and squeezed out between two padding rollers, the weight increase being about 100%, and then steamed continuously for 40 minutes in a steamer, using saturated steam at 102°–103° C. Thereafter, the dyeing is again rinsed with warm water having a temperature of 50° C. An excellent grey dyeing with very good fastness to perspiration, milling, washing and hot water, is obtained.

EXAMPLE 12

The procedure followed is an indicated in Example 11, but with the difference that instead of the compound given there, 10 parts of the compound from Example 7 are employed.

A grey dyeing which has no frosting effect is also obtained with this compound.

EXAMPLE 13

10 parts of the 1:2 chromium complex of the dyestuff 2-amino-phenol-4-ethylsulphone→1-methylsulphonylamino-7-hydroxynaphthalene are dissolved in 600 parts of hot, soft water having a temperature of 80° C.; a mixture of 8 parts of the compound from Example 2 and 2 parts of the compound of the following formula

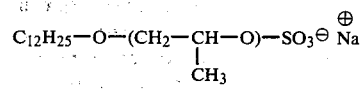

and 2 parts of diethylene glycol monobutyl ether is then added. The solution is added to 200 parts of a 4% strength aqueous formulation of a commercially available derivative of carob bean flour, whilst stirring continuously. Thereafter, 20 parts of acetic acid (60% strength) are added to the homogeneous solution. The dyestuff formulation is then filled up to 1,000 parts with cold, soft water.

A sliver of polyamide 6 fibres is padded with this dye liquor, the liquor pick-up being about 80%, and then steamed continuously for 15 minutes in a steamer at 102°–103° C. Thereafter, the sliver is washed with warm water having a temprature of 50° C. on a back-washer and rinsed. A very uniform grey dyeing with very good fastness to light washing and perspiration is obtained.

EXAMPLE 14

10 parts of the compound from Example 2 and 3 parts of sodium laurylsulphonate and 2 parts of benzyl alcohol are added to a mixture of 20 parts of the dyestuff according to C.I. 15,710 (3rd edition, volume 4) and 500 parts of soft water having a temperature of about 90° C., whilst stirring, and the mixture is then added to 100 parts of a 4% strength aqueous formulation of a commercially available derivative of carob bean flour. Thereafter, the solution is cooled to about 50° C. and a mixture of 12 parts of chromium fluoride, 20 parts of formic acid (85strength) and 100 parts of hot water is added. Finally, the dyestuff formulation is filled up to 1,000 parts with cold, soft water.

A wool sliver is printed with this printing paste on a Vigoureux printing machine (50:50 roller) and then steamed for 20 minutes in a pressure steamer using saturated steam at about 108° C. Thereafter, the sliver is washed with warm water having a temperature of 50° C. on a back-washer, rinsed and acidified with formic acid.

A black print with very good fastness to light and wet processing is obtained in this manner.

EXAMPLE 15

500 parts of soft water having a temperature of 70° C. are poured over 5 parts of the 1:2 chromium complex of the monoazo dyestuff anthranilic acid→1-phenyl-3-methyl-pyrazolone; a mixture of 4 parts of the compound from Example 5 and 2 parts of sodium laurylsulphonate and 2 parts of the compound of the following formula

is then added. The mixture is heated to 80°–90° C. and added to 100 parts of a 4% strength aqueous formulation of a commercially available derivative of carob bean flour, whilst stirring vigorously. Thereafter, 5 parts of acetic acid (60% strength) are added to the solution, whilst stirring. The dye liquor which has now formed is then filled up to 1,000 parts with soft water. This dye liquor is applied uniformly to a polyamide 6,6 tufted carpet by means of an applicator, the weight increase being about 300%, and the carpet is then steamed continuously for 15 minutes in a steamer using saturated steam at 102°–103° C. Thereafter, it is washed with warm water having a temprature of 50° C. on a continuous open-width washing machine and rinsed.

A very uniform yellow dyeing which contains no frosting effect and has very good fastness to light, water and shampoo, is obtained.

EXAMPLE 16

10 parts of the dyestuff of the following formula

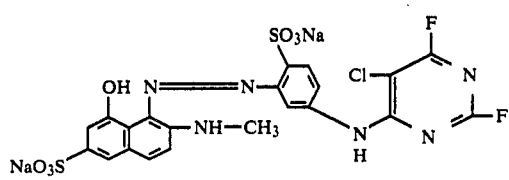

are dissolved in 600 parts of hot, soft water having a temperature of 80° C.; 8 parts of the compound from Example 2 and 2 parts of sodium laurylsulphonate and 2 parts of the compound of the following formula

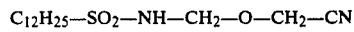

are then added. The solution is added to 200 parts of a 4% strength aqueous formulation of a commercially available derivative of carob bean flour, whilst stirring continuously. Thereafter, 5 parts of acetic acid (60% strength) are added to the homogeneous solution. Finally, the dyestuff formulation is filled up to 1,000 parts with cold, soft water. A wool gaberdine is impregnated with this dye liquor on a padder; the weight increase is about 80%. The gaberdine is then steamed continuously for 15 minutes in a steamer using saturated steam at 102°–103° C. Thereafter, the dyeing is washed with warm water, which has a temperature of 50° C. and a pH value of about 8.5, rinsed and acidified with acetic acid or formic acid.

A brilliant red dyeing which contains no frosting effect is obtained.

EXAMPLE 17

20 parts of the dyestuff according to C.I. 58,005 (3rd edition, volume 4) are dissolved in 600 parts of hot, soft water having a temperature of 80° C.; a mixture of 10 parts of the compound from Example 1 and 4 parts of sodium laurylsulphonate and 2 parts of ethylene glycol monobutyl ether is then added. The solution is added to 200 parts of a 4% strength aqueous formulation of a commercially available derivative of carob bean flour, whilst stirring vigorously. Thereafter, the solution is cooled to about 50° C. and a mixture of 20 parts of chromium fluoride, 30 parts of formic acid (85% strength) and 100 parts of hot water is added. Finally, the dyestuff formulation is filled up to 1,000 parts with cold, soft water.

Loose wool is impregnated with the dyestuffs obtained in this manner and squeezed out between two padding rollers, the weight increase being about 120%, and then steamed continuously for 45 minutes in a steamer using saturated steam at 102°–103° C. Thereafter, the dyeing is again rinsed with warm water having a temperature of 50° C.

An excellent bluish-tinged red dyeing with very good fastness to perspiration, water and washing, is obtained.

EXAMPLE 18

15 parts of the disperse dyestuff of the following formula

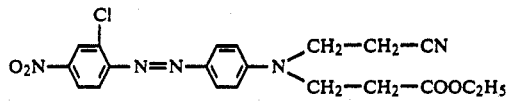

are sprinkled into 500 parts of warm water, which has a temperature of 50° C. and contains 12 parts of the compound from Example 7, whilst stirring vigorously. The dispersion is added to 200 parts of a 4% strength aqueous formulation of a commercially available derivative of carob bean flour, whilst stirring continuously. Thereafter, 5 parts of acetic acid (60% strength) are added to the dyestuff formulation, whilst stirring. Finally, the formulation is filled up to 1,000 parts with cold water.

A fabric made of polyethylene terephthalate is impregnated with this dye liquor on a padder, the liquor pick-up being about 60%, and is steamed for 5 minutes in a pressure steamer at 135° C. Thereafter, the dyeing is rinsed again with warm water having a temperature of about 50° C.

A very uniform scarlet dyeing is obtained in this manner.

EXAMPLE 19

10 parts of the dyestuff C.I. 48,040 (3rd edition, volume 4) are dissolved in 350 parts of hot, soft water, which has a temperature of 90° C. and contains 1 part of acetic acid (60% strength).

6 parts of the dyestuff C.I. 40,215 (3rd edition, volume 4) are also dissolved in 350 parts of hot, soft water having a temperature of 90° C. First the last-mentioned dyestuff solution and then the solution of the cationic dyestuff are added to 75 parts of a 4% strength aqueous formulation of a commercially available derivative of carob bean flour, which contains 10 parts of the compound from Example 2, whilst stirring. Finally, the dyestuff formulation is filled up to 1,000 parts with cold, soft water.

A furniture upholstery material consisting of polyacrylonitrile fibres (pile) and cotton (backing) is impregnated with the dye liquor described above on a padder, the liquor pick-up being about 100%. The material is then steamed continuously for 15 minutes in a steamer at 102°–103° C. Thereafter, the dyeing is rinsed again with water having a temperature of 50° C. on a continuous open-width washing machine.

An outstanding yellow dyeing which exhibits no frosting effect is obtained.

EXAMPLE 20

8 parts of the dyestuff C.I. 51,004 (3rd edition, volume 4) are dissolved in 350 parts of hot, soft water which has a temperature of 90° C. and contains 1 part of acetic acid (60% strength).

6 parts of the dyestuff of the following formula

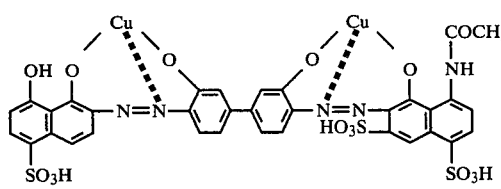

are also dissolved in 350 parts of hot, soft water having a temperature of 90° C. First the last-mentioned dyestuff solution and then the solution of the cationic dyestuff are added to 75 parts of a 4% strength aqueous formulation of a commercially available derivative of carob bean flour, which contains 7 parts of the compound from Example 1 and 3 parts of sodium laurylsulphonate and 2 parts of triacetin, whilst stirring. Finally, the dyestuff formulation is filled up to 1,000 parts with cold, soft water.

An upholstery plush, consisting of polyacrylonitrile fibres (pile) and cotton (backing) is impregnated with the abovementioned dye liquor on a padder, the liquor pick-up being about 100%. It is then steamed continuously for 15 minutes in a steam at 102°–103° C. Thereafter, the dyeing is rinsed again with warm water having a temperature of 50° C. on a continuous open-width washing machine. An excellent blue dyeing which exhibits no frosting effect is obtained.

We claim:

1. A surface-active ester of a polyhydroxy compound selected from the group consisting of glycerol, erythritol, sorbitol, erythrose, arabinose, xylose, glucose, fructose, galactose, mannose, maltose, polyvinyl alcohols, sucrose, tetralose, raffinose and, alkyl or hydroxyalkylglycosides, and an acylaminocarboxylic acid of the formula

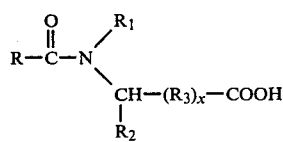

in which
R represents H, $C_1$–$C_4$-alkyl, $C_1$–$C_{22}$-alkoxy, $C_3$–$C_{22}$-alkenoxy, aryl, aralkyl, aroxy, aralkoxy or the radical

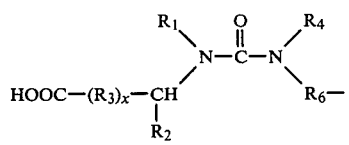

$R_1$, $R_4$ and $R_5$ represent H, $C_1$–$C_{22}$-alkyl, $C_3$–$C_{22}$-alkenyl, cycloalkyl, aryl or aralkyl, or
$R^6$ represents $C_2$–$C_8$-alkylene or a radical of the formula

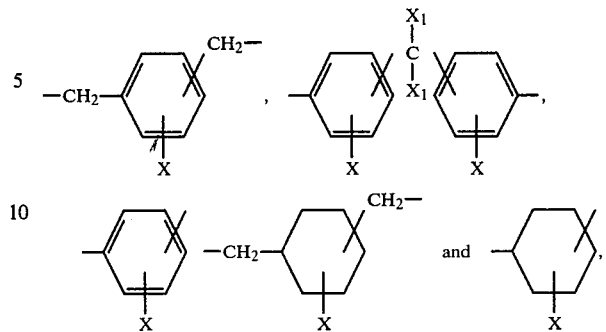

$R_2$ represents H, COOH, COO $C_1$–$C_4$-alkyl or $C_1$–$C_6$-alkyl,
$R_3$ represents $C_1$–$C_{10}$-alkylene and
x represents 0 or 1,
wherein at least one of the radicals $R_1$ to $R_5$ contains at least 6 carbon atoms, and wherein the alkyl, alkenyl and cyclic radicals may be substituted by fluorine, chlorine, bromine, cyano, carboxyl, $C_1$–$C_4$-alkoxy and the cyclic radicals may also be substituted by $C_1$–$C_4$-alkyl, the total number of carbon atoms being 20 to 60 when $R_5$ is

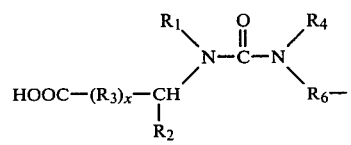

and being 12 to 30 when $R_5$ is H, $C_1$–$C_{22}$-alkenyl, cycloalkyl, aryl or aralkyl.

2. A surface active ester according to claim 1, in which
R' represents hydrogen, $C_1$–$C_4$-alkyl, $C_1$–$C_{22}$-alkoxy, $C_3$–$C_{22}$-alkenyloxy, phenyl, naphthyl, benzyl, phenylethyl naphthylmethyl, phenoxy, benzoxy, phenylethoxy or a radical

$R_1'$, $R_4'$ and $R_5'$ represent hydrogen, $C_1$–$C_{22}$-alkyl, $C_3$–$C_{22}$-alkenyl, cyclohexyl, tetrahydronaphthyl, decahydronaphthyl, abietyl, phenyl, naphthyl, benzyl or phenylethyl or
$R_5'$ represents a radical of the formula

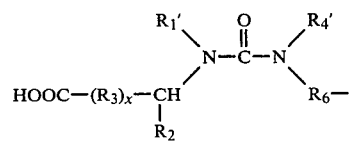

$R_6$ represents $C_2$–$C_8$-alkylene or a radical of the formulae

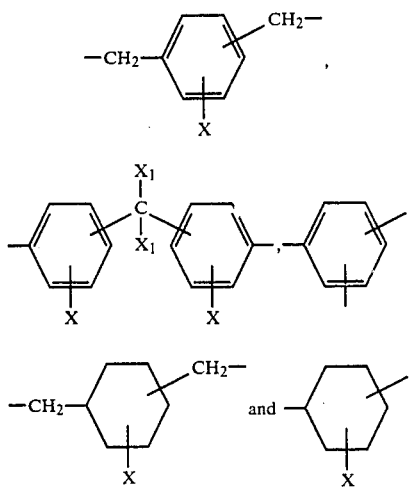

X and $X_1$ represent hydrogen or $C_1$-$C_4$-alkyl, and at least one of $R_1'$, $R_2$, $R^3$, $R_4'$ and $R_5'$ contains at least 6 carbon atoms.

3. A surface active ester according to claim 1, in which the acylaminocarboxylic acid is of the formula

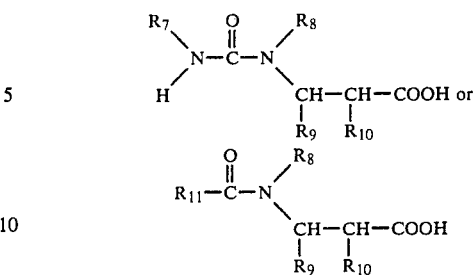

wherein
$R_7$ represents $C_1$-$C_{22}$-alkyl, $C_3$-$C_{22}$-alkenyl, cyclohexyl, tetrahydronaphthyl, decahydronaphthyl, abietyl, phenyl,
$R_8$ represents hydrogen, $C_1$-$C_{22}$-alkyl, $C_3$-$C_{22}$-alkenyl, cyclohexyl, tetrahydronaphthyl, decahydronaphthyl, abietyl, benzyl or phenylethyl,
$R_9$ represents hydrogen or carboxyl and
$R_{10}$ and $R_{11}$ represent hydrogen or methyl, at least one of the radicals $R_7$ or $R_8$ has at least 8 carbon atoms and the alkyl, alkenyl and cyclic radicals can be substituted by fluorine, chlorine, bromine, cyano, carboxyl, $C_1$-$C_4$-alkoxycarbonyl, carbamoyl or $C_1$-$C_4$-alkoxy and the cyclic radicals can also be substituted by $C_1$-$C_4$-alkyl.

4. A surface-active ester according to claim 1, in which the polyol is sorbitol, glucose, alkyl- or hydroxyalkylglycosides, tetralose, raffinose or sucrose.

* * * * *